United States Patent [19]

Mori et al.

[11] Patent Number: 5,731,193
[45] Date of Patent: Mar. 24, 1998

[54] RECOMBINANT DNA AND TRANSFORMANT CONTAINING THE SAME

[75] Inventors: Tetsuya Mori, Kyoto; Kozo Yamamoto; Tsunetaka Ohta, both of Okayama, all of Japan

[73] Assignee: Kabushiki Kaisha Hayashibara Seibutsu Kagaku Kenkyujo, Okayama, Japan

[21] Appl. No.: 828,511

[22] Filed: Mar. 31, 1997

Related U.S. Application Data

[63] Continuation of Ser. No. 355,245, Dec. 9, 1994, abandoned.

[30] Foreign Application Priority Data

Dec. 15, 1993 [JP] Japan ................................. 5-342237

[51] Int. Cl.$^6$ ............................ C12N 15/85; C12N 15/67; C12P 21/02; C07H 21/04
[52] U.S. Cl. ................... 435/320.1; 435/69.1; 435/69.51; 435/69.6; 435/70.3; 435/70.5; 435/172.1; 536/23.5; 536/23.52; 536/24.1
[58] Field of Search ..................... 435/320.1, 69.1, 435/69.5, 69.51, 69.6, 69.4, 70.1, 70.3, 70.5, 172.1; 536/24.1, 23.1, 23.51, 23.52; 935/27, 33, 35, 66, 70, 43

[56] References Cited

U.S. PATENT DOCUMENTS

| | | | |
|---|---|---|---|
| 4,377,513 | 3/1983 | Sugimoto et al. | 530/395 |
| 4,703,008 | 10/1987 | Lin | 435/240.2 |
| 4,716,112 | 12/1987 | Panayotatos | 435/69.1 |
| 4,808,523 | 2/1989 | Revel et al. | 435/69.51 |
| 4,894,334 | 1/1990 | Ben-Bassat et al. | 435/69.1 |
| 4,921,699 | 5/1990 | De Chiara et al. | 435/85.7 |
| 4,939,088 | 7/1990 | Young et al. | 435/69.51 |
| 5,089,397 | 2/1992 | Kushner et al. | 435/69.1 |
| 5,096,705 | 3/1992 | Goeddel et al. | 424/85.5 |
| 5,362,490 | 11/1994 | Kurimoto et al. | 424/85.5 |

FOREIGN PATENT DOCUMENTS

| | | |
|---|---|---|
| 0123372 | 1/1984 | European Pat. Off. |
| 2657880 | 9/1991 | France. |
| 2146031 | 4/1985 | United Kingdom. |
| 8102425 | 9/1981 | WIPO. |
| 8502624 | 6/1985 | WIPO. |
| 9320218 | 10/1993 | WIPO. |

OTHER PUBLICATIONS

Weidle, U. et al., "The 5' flanking region of a human INF-alpha gene mediates viral induction of transcription", Nature, vol. 303, No. 2, Jun. 1983, pp. 442–446.

Henco, K. et al., "Structural relationship of human interferon alpha genes and pseudogenes", Journal of Molecular Biology, vol. 185, 1985, pp. 227–260.

Recny, M. A. et al., "Structural characterization of natural human urinary and recombinant DNA-derived erythroprotein", The Journal of Biological Chemistry, vol. 262, No. 35, Dec. 1987, pp. 17156–17163.

Tanaka et al., "Cytokine gene regulation: regulatory cis-elements and DNA-binding factors involved in the interferon system", Advances in Immunology, vol. 52, 1992, pp. 263–281.

Ryals et al., "A 46-nucleotide promoter segment from an IFN-alpha gene renders an unrelated promoter inducible by virus", Cell, vol. 41, Jun. 1985, pp. 497–507.

Abstract, Database WPI, Section Ch, Week 8617, Derwent Publications Ltd., London, GB; Class B04, AN 86–109964, XP002016726 & JP–A–61 052 286 (Toray Ind Inc), Mar. 14, 1986.

Mori et al., "A high-level and regulatable production system for recombinant glycoproteins using a human interferon-alpha promoter-based expression vector", Gene, vol. 144, No. 2, Jul. 8, 1994.

Craig, E.A. et al.; "Sequence Organization of Two Recombinant Plasmids Containing Genes for the Major Heat Shock-Induced Protein of *D. melanogaster*"; Cell, vol. 16, pp. 575–599 (1979).

Brinster, R.L. et al.; "Somatic Expresion of Herpes Thymidine Kinase In Mice Following Injection Of A Fusion Gene Into Eggs"; Cell, vol. 27, pp. 223–231, (1981).

Lee, F. et al.; Glucocorticoids Regulate expression Of Dihydrofolate Reductase cDNA In Mouse Mammary Tumour Virus CHimaeric Plasmids; Nature, vol. 294, pp. 228–232, (1981).

Fukunaga et al. "Constitutive Production of Human Interferons by Mouse Cells ... " PNAS 81 5086–5090 1984.

Mori et al. "A High Level & Regulatable Production System for Recombinant Glycoproteins ... " Gene 144 289–293 1994.

Dron et al. "Priming Affects the Activity of a Specific Region of the Promoter of the Human Beta Interferon Gene" Mol Cell Biol 10(2) 854–858 1990.

*Primary Examiner*—David Guzo
*Assistant Examiner*—Nancy J. Degen
*Attorney, Agent, or Firm*—Browdy and Neimark

[57] ABSTRACT

Insertion of IFN-alpha promoters in recombinant DNAs improves their expression efficiencies for useful polypeptides. Expression of such a recombinant DNA in host cells of mammalian origin is artificially controllable by the presence and absence of external stimuli using IFN-alpha inducers. Thus, transformants with such a recombinant DNA readily increase to a maximized cell density with causing neither damages nor extinction due to polypeptides they produce, and subsequent exposure to IFN-alpha inducers allows the proliferated cells to efficiently produce polypeptides with significant glycosylations.

16 Claims, 1 Drawing Sheet

RECOMBINANT DNA AND TRANSFORMANT CONTAINING THE SAME

This application is a continuation of application Ser. No. 08/355,245, filed Dec. 9, 1994, now abandoned.

BACKGROUND OF THE INVENTION

1. Field of the Invention

This invention relates to a novel recombinant DNA and a transformant containing the same, in particular, to a recombinant DNA which enables artificial control on expression for useful polypeptides, as well as to a transformant comprising a host cells of mammalian origin wherein such recombinant DNA has been introduced.

2. Description of the Prior Art

Recent advances in recombinant DNA technology are very striking. Nowadays even polypeptides which are present in trace in living bodies can be easily produced in desired amounts by application of recombinant DNA technology. The typical models are insulin and IFN and in recent various types of recombinant polypeptides are in practical uses or clinical tests.

Recombinant polypeptides are usually produced by introducing DNAs which code such a polypeptide in host microorganisms such as *Escherichia coli* to make transformants, cultivating them and purifying the resultant cultures. This method has the merit that one can easily obtain transformants with high efficiencies when he or she carefully constructs recombinant DNAs, as well as the demerit that glycosylated polypeptides are however unobtainable therewith because microorganisms lack abilities of glycosylating polypeptides. Researches in the last several years revealed that in certain lymphokines and cytokines glycosylation may have an important influence on their efficacies and possible side effects. While, unlike microorganisms, host cells of mammalian origin physiologically effect glycosylation: Thus recently cells from mammals including human have been revaluated as substituent host for microorganisms.

By the way, to allow DNAs to efficiently express in hosts, it is necessary to link strong promoters thereto. A variety of promoters have been devised hitherto, which can be briefly divided into two types: One type is such which constitutively expresses characteristics, while the other type inducibly expresses on external stimuli. Generally in transformants, dependently on hosts, produced polypeptides may damage hosts to consequently reduce expression efficiencies of DNAs or under certain circumstances to result in no expression of even in death of hosts. Because of these, the use of the latter type of promoters, i.e. those whose expression is controllable by external stimuli, is preferable.

Examples of conventional promoters which are known to inducibly express on external stimuli are mouse mammary gland tumor virus promoter, metallothionein promoter and heat-shock proteins. These promoters have the merit that they enable artificial control on expression of DNAs, as well as having the drawback that they generally exhibit decreased expressing abilities and need external stimuli by steroid hormones and heavy metals. Many steroid hormones and heavy metals however exhibit distinct biological activities and toxicities in living bodies and this hinders their uses in production of recombinant polypeptides which are principally directed to administration to human. Although induction of expression by heating is superior because it does not add such a substance in production systems, researches on heat-shock protein promoters have just begun and therefore no promoters only with a sufficiently high expressing ability have been developed.

Abbreviations

Throughout the specification and figure, interferon is abbreviated as "IFN"; interferon-alpha, "IFN-alpha"; interferon-alpha promoter, "IFN-alpha promoter"; human interferon-alpha promoter, "HuIFN-alpha promoter"; human interferon-alpha2 promoter, "hIFP"; erythropoietin, "EPO"; human erythropoietin, "hEPO"; human interferon-gamma, "HuIFN-gamma"; neomycin amino-glycoside phosphotransferase gene, "NeoR gene"; dihydrofolate reductase gene, "dhfr gene"; beta-lactamase gene, "AmpR gene"; SV40 enhancer, "SVE"; polyadenylylation signal region from SV40 virus, "poly (A) region"; replication initiating site in M13 phage, "M13"; and replication initiating site in *Escherichia coli*, "ORI";

SUMMARY OF THE INVENTION

In view of the foregoing, one object of this invention is to provide a replicable recombinant DNA which enables artificial control on expression for useful polypeptides.

Another object of this invention is to provide a transformant comprising a host cell of mammalian origin wherein such recombinant DNA has been introduced.

This invention solves the first object with a replicable recombinant DNA comprising a plasmid vector which links an IFN-alpha promoter, and a DNA which codes a polypeptide excluding IFN-alpha.

This invention solves the second object with a transformant comprising a host cell of mammalian origin wherein such replicable recombinant DNA has been introduced.

The recombinant DNA of this invention expresses production of objective polypeptides when one introduces it in appropriate host cells of mammalian origin to make transformants and then cultures the transformants while stimulating them with IFN-alpha inducers.

The transformant of this invention produces objective polypeptides when cultivated while stimulating with IFN-alpha inducers.

BRIEF EXPLANATION OF THE FIGURES

In FIG. 1, the symbol SVE3 designates a gene wherein 3 SVEs are linked in series.

DETAILED DESCRIPTION OF THE INVENTION

Figure 1:
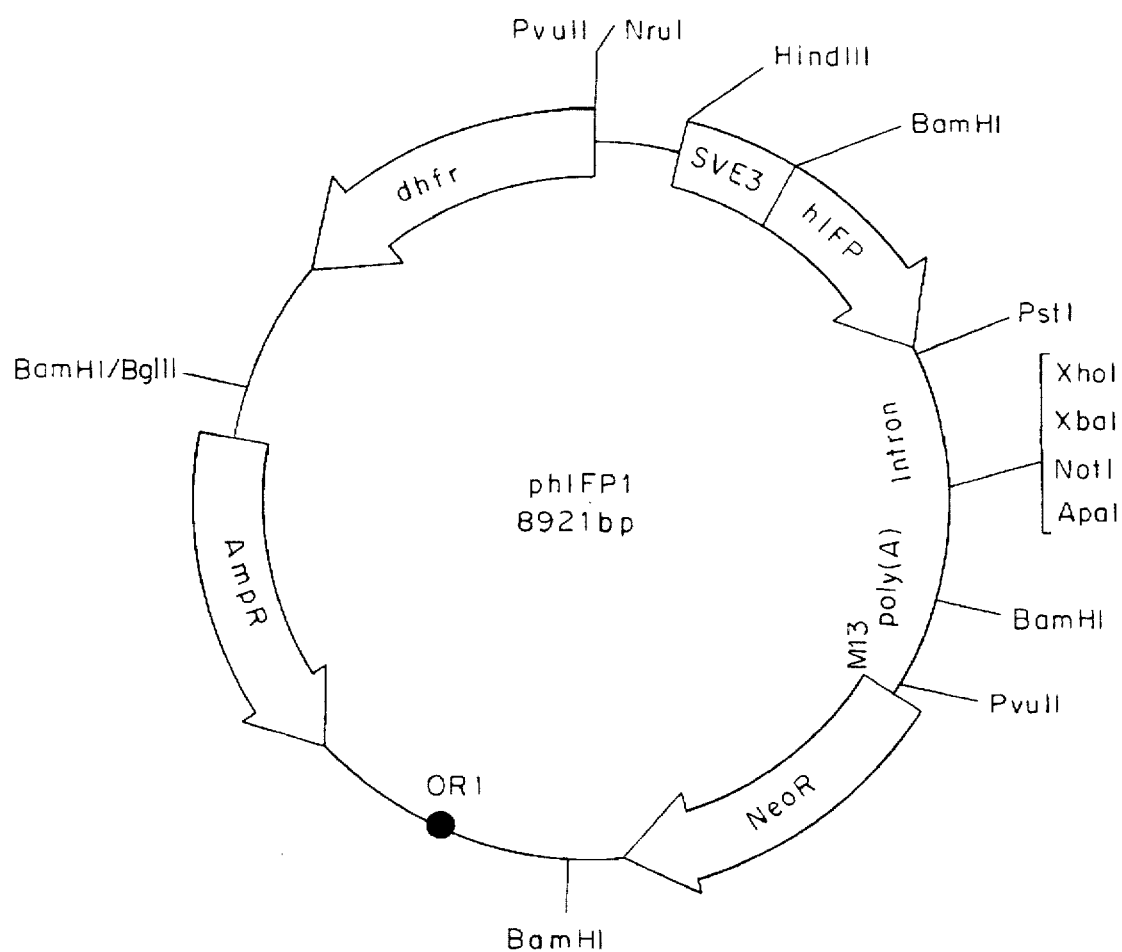
FIG. 1 shows the structure of plasmid vector phIFP1.

Now explaining this invention in conjunction with Experiments and Examples, the recombinant DNA of this invention comprises a plasmid vector which links an IFN-alpha promoter and a DNA which codes a polypeptide excluding IFN-alpha.

The wording "IFN-alpha promoter" as referred to in this invention means all the promoters capable of promoting expression of DNAs which code IFN-alpha. Several types of IFN-alpha promoters from different origins are known: For example, there are about 20 distinct types of HuIFN-alpha promoters including HuIFN-alpha2 and HuIFN-alpha8 promoters. Also, in animals such as mouse and rat, similar types of promoters are present and feasible in this invention similarly as HuIFN-alpha promoters. However, in case of producing polypeptides which are principally incorporated in medicines and administered to human, it is preferable to use HuIFN-alpha promoters which are in itself present in human body. The nucleic acid sequence starting at 5'-terminal of hIFP is given in the Sequence Listing with SEQ ID No.1.

IFN-alpha promoters are obtainable from mammalian cells with methods which are common in the art. For example, genomic DNAs are collected from IFN-alpha producer cells such as leukocyte and lymphoblastoid cells and subjected to gene amplification by the PCR method in the presence of a primer which bears a nucleic acid sequence with IFN-alpha promoter region. The obtained DNA fragments are introduced in an appropriate vector to make a recombinant DNA which is then proliferated in an appropriate host such as *Escherichia coli*, followed by collecting the recombinant DNA from the resultant culture. Subsequent cleavage of the recombinant DNA by appropriate restriction enzymes yields a DNA fragment with IFN-alpha promoter region. Plasmid vectors feasible in this invention link such an IFN-alpha promoter, which are usually created in artificial manner by arbitrarily linking DNA fragments as described above with DNAs which code polypeptides other than IFN-alpha and also with drug resistance genes using restriction enzymes and DNA ligases in combination.

The plasmid vector in this invention does not exclude insertion of appropriate drug resistance genes which are to clone recombinant DNAs and transformants, as well as of appropriate enhancers which are to improve expression efficiencies in transformants. Particular drug resistance genes are, for example, NeoR gene which imparts resistance against G-418 (a type of protein synthesis inhibitor), dhfr gene which imparts resistance against methotrexate (a type of nucleic acid synthesis inhibitor) and AmpR gene which imparts resistance against ampicillin. One of suitable enhancers is SVE: The below-mentioned plasmid vector phIFP1, which bears all of these drug resistance genes and enhancer, is very useful in practice of this invention. Of course one can insert in appropriate sites in such a plasmid vector initiation and termination codons.

Now explaining DNAs which code polypeptides excluding IFN-alpha, the wording "polypeptide" as referred to in this invention means polypeptides in general excluding IFN-alpha and this invention is applicable to even polypeptides wherein glycosylation has a substantial influence on their biological activities and/or possible side effects. Particular polypeptides are cytokines such as IFN-beta, IFN-gamma, tumor necrosis factors, macrophage migration inhibitory factor, macrophage activating factor, colony forming factor, blastogenetic factor, interleukin 2, interleukin 3, neutrophil chemotactic factor and leukocyte migration inhibitory factor, peptide hormones such as EPO, insulin, somatostatin and growth hormone, and enzymes such as tissue plasminogen activator. It is known that many polypeptides among these are originally produced in glycosylated forms and in several substances glycosylation actually has a substantial influence on their biological activities and possible side effects. The HuIFN-gamma, tumor necrosis factors and hEPO produced by transformants according to this invention bear significant glycosylations and therefore exhibit notable therapeutic and prophylactic effects in human without causing serious side effects when incorporated in medicines and administered to human.

The wording "polypeptide" as referred to in this invention means those as described above. Thus the wording "DNA which codes a polypeptide excluding IFN-alpha" as referred to in this invention means DNA and DNA fragments, usually, those in cDNA form, which code such a polypeptide or its homologous mutants. Generally cDNAs have the merit that they are easily available in desired amounts and readily inserted in plasmid vectors with no special pretreatments. By inserting such a cDNA in plasmid vectors using restriction enzymes and DNA ligases in combination, recombinant DNAs according to this invention can be obtained. Such a recombinant DNA is replicable and therefore easily obtainable in desired amounts by allowing it to proliferate in microorganisms such as *Escherichia coli*.

The transformant of this invention comprises a host cell of mammalian origin where a recombinant DNA as described above has been introduced. Such a host cell is feasible with cells which are common in the art and in this invention there are no limitations in their sources or origins as long as the recombinant DNA can be introduced therein and the resultant transformants produce objective polypeptides on external stimuli. General host cells are, for example, blood fetal stem cells, lymphocytes, fibroblast cells, oocytes and mutant cells thereof which are arbitrarily chosen dependently on the type of objective polypeptide and the nature and properties of recombinant DNA to be used. Depending on the use of objective polypeptide, there may be inevitably provided restrictions in sources and origins of host cells: For example, in the case of polypeptides which are incorporated in medicines and then administered to human, it is preferable to use host cells of human origin. Particular host cells are, for example, CHO cell (ATCC CCL61) of Chinese hamster origin, BALL-1 cell (JCRB 003578) of acute lymphoblastic leukemia origin and Namalwa cell (ATCC CRL1432) of Burkitt's lymphoma origin and among these lymphoblastoid cells including BALL-1 cell are the best host for large-scale production of useful polypeptides because they readily yield transformants with high expression efficiencies and highly susceptible to proliferation. To introduce the recombinant DNA of this invention in such a host cell, for example, usual DEAE-dextran method, calcium phosphate cosedimentation method, electroporation, lipofection, protoplastic fusion with *Escherichia coli*, microinjection and infectious virus vector method are feasible.

Now explaining the way of using the transformant of this invention, to produce polypeptides therewith, dependently on the amount needed, the transformant is first proliferated to give a required cell density, then allowed to produce polypeptides by culturing while stimulating with IFN-alpha inducers.

The transformant of this invention can be proliferated by methods common in the art. For example, the transformant is suspended in culture media to give a cell density of about $1 \times 10^5 - 1 \times 10^7$ cells/ml and then cultured around 37° C. for about one day to one week in usual manner while arbitrarily refreshing the culture media, thus increasing the transformant by about 2–200-folds. Proliferation of transformants using lymphoblastoid cells as host is much easier: For example, transformants are subcutaneously or intraperitoneally implanted in an inoculum of about $1 \times 10^6 - 1 \times 10^9$ cells/animal in newborn rodents such as mouse, nude mouse, nude rat and hamster which had been arbitrarily injected with rabbit anti-thymocyte serum to weaken possible immunoreactions. By subsequently feeding the animals in usual manner for about 2–10 weeks, tumor lumps of the transformant are formed in the animals. The tumor masses are collected, disaggregated, washed in appropriate media and then used to produce polypeptides. Such in vivo proliferation using non-human warm-blooded animals readily yields about 2–10,000-fold cell population of transformants. Proliferation using non-human warm-blooded animals is detailed in Japanese Patent Publication No.54,158/81.

Transformants thus obtained intra- and/or extracellularly produce polypeptides when cultured while stimulating with IFN-alpha inducers. This invention provides no special limitations in IFN-alpha inducers: Usually, viral inducers such as Sendai virus, Newcastle disease virus and vaccinia virus and double-stranded RNAs are used. Depending on the type of polypeptide, generally, transformants intra- and/or extracellularly produce polypeptides when cultured at about 35°–37° C. for about 10–20 hours in the presence of such an inducer. At this time, if transformant are simultaneously or successively exposed to both an IFN-alpha inducer and an appropriate amount of IFN-alpha, then production of polypeptides by transformants may be notably augmented. Depending on the types of polypeptide and host cell, the amount of IFN-alpha inducer to be added to culture media usually lies within the range of about 0.1–50,000 hemagglutination titers/ml for viral inducers, desirably, about 10–500 hemagglutination titers/ml, while for double-stranded RNAs, about 1–100 micrograms/ml, desirably, about 10–50 micrograms/ml. The amount of IFN-alpha to be used in combination with IFN-alpha inducers usually lies within the range of about 0.1–10,000 IU/ml, desirably, about 100–1,000 IU/ml. Amounts of IFN-alpha lower than this range hardly give a notable effect, while amounts higher than this range may affect subsequent purification: Thus the above range is deemed to be best.

Produced polypeptides can be purified by methods common in the art. For example, supernatants which have been obtained by centrifugally removing transformants from cultures are added with ammonium sulfate to effect salting out and the resultant sediments with crude polypeptides are purified by purification methods, for example, concentration, salting out, dialysis, column chromatography, high-performance liquid chromatography, gel electrophoresis, isoelectric point electrophoresis and affinity chromatography which may be arbitrarily combined. In case that objective polypeptides are IFNs and tumor necrosis factors, affinity chromatographies using monoclonal antibodies as ligand are very useful and polypeptides with the possible highest purity can be obtained with minimized labor and cost.

Polypeptides thus obtained bear significant glycosylation due to postexpression modifications in hosts. Because of this, it can be said that this invention favorably utilizes recombinant DNA technology to give polypeptides which are much more similar in nature and properties to correspondent natural polypeptides.

The recombinant DNA and transformant of this invention will be concretely explained in conjunction with several embodiments. The procedures used in the following Examples are common in the art and detailed, for example, in J. Sambook et al., *Molecular Cloning A Laboratory Manual*, 2nd edition, 1989, Cold Spring Harbor Laboratory, Cold Spring Harbor, N.Y., U.S.A., and Ausubel et al., *Current Protocols in Molecular Biology*, 1990, John Wiley & Sons Ltd., Sussex, UK.

EXAMPLE 1
Recombinant DNA with hEPO DNA

This Example is to illustrate recombinant DNA which contains a DNA coding hEPO as non IFN-alpha polypeptide. The recombinant DNA in this Example, which is created by inserting hEPO-coding cDNA in plasmid vector phIFP1, is readily introduceable in host cells of mammalian origin including human lymphoblastoid cells and sensitive to external stimuli to exhibit a high expression efficiency.

EXAMPLE 1-1
Preparation of plasmid vector phIFP1

Plasmid vector phIFP1 was created by linking in the given order a Bam HI-Pst I DNA fragment of 508 base pairs with hIFP region, a Pst I-Xho I DNA fragment of 840 base pairs with human beta-globin intron, a Xho I-Bam HI DNA fragment of 320 base pairs with poly (A) region, a Bam HI-Pvu II DNA fragment of 467 base pairs with M13, a Pvu II-Bgl II DNA fragment of 1,487 base pairs with NeoR gene, a Bam HI-Bgl II DNA fragment of 2,230 base pairs of with both ORI and AmpR gene, a Bam HI-Pvu II DNA fragment of 1,907 base pairs with dhfr gene, a Nde I-Hind III DNA fragment of 227 base pairs, a Nde I-Hind III DNA fragment of 214 base pairs, and a Hind III-Bam HI DNA fragment of 684 base pairs wherein 3 SVE genes were linked in series. FIG. 1 shows the structure of plasmid vector phIFP1. The following will illustrate preparation of these DNA fragments.

EXAMPLE 1-1(a)
Preparation of DNA fragment with hIFP region

About $1\times10^8$ BALL-1 cells which had been proliferated in usual manner were washed in chilled PBS and then exposed to both proteinase K and SDS in chilled $TNE_{100}$ while gently stirring. The reaction mixture was incubated at 50° C. for 15 hours, washed with a mixture solution of phenol and chloroform, dialyzed against TE solution, added with an appropriate amount of ribonuclease and incubated at 37° C. for 30 minutes. Thereafter the resultant was added with appropriate amounts of SDS and proteinase K, incubated at 37° C. for additional 3 hours, washed with a mixture solution of phenol and chloroform, concentrated with n-butanol and dialyzed against TE solution, thus obtaining a purified genomic DNA.

Separately Primers 1 and 2 as shown in Tables 1 and 2 respectively which beared a nucleic acid sequence with hIFP gene as shown in the Sequence Listing with SEQ ID No.1 were synthesized in usual chemical manner and the genomic DNA was subjected to gene amplification by the PCR method in the presence of these Primers to obtain a DNA fragment of about 500 base pairs with hIFP region. The DNA fragment was then exposed in usual manner to T4 DNA polymerase for smoothing both ends and inserted in plasmid vector pUC18 (ATCC37253) which had been treated with restriction enzyme Hinc II. The obtained recombinant DNA was introduced by the competent cell method in HB101 strain of *Escherichia coli* (ATCC33694) which was then inoculated in LB medium (pH7.2) containing 100 micrograms/ml ampicillin, cultivated at 37° C. for 18 hours and centrifugally collected from the resultant culture, followed by extracting the recombinant DNA by usual methods. A portion of the recombinant DNA was investigated by the dideoxy method for nucleic acid sequence in the inserted DNA fragment, confirming that the recombinant DNA contained the nucleic acid sequence as shown in the Sequence Listing with SEQ ID No.1. Thereafter the recombinant DNA was digested with restriction enzymes Bam HI and Pst I and subsequent purification of the digest gave a Bam HI-Pst I DNA fragment of 508 base pairs with hIFP region.

TABLE 1

Primer 1:
5'-GGATCCCGCCTCTTATGTACCCACAAAAATC-3'(SEQ ID NO: 2)

TABLE 2

Primer 2:
5'-GACGTCAGACTGGTTGAAATGGGTGAGCCTA-3'(SEQ ID NO: 3)

EXAMPLE 1-1(b)

Preparation of DNA fragment with human beta-globin intron region

With reference to the nucleic acid sequence for human beta-globin intron reported by S. L. Thein et al. in *Proceedings of the National Academy of Sciences, USA*, Vol.87, pp.3,924–3,928 (1990), Primers 3 and 4 with nucleic acid sequences as shown in Tables 3 and 4 respectively wherein the B region was sandwiched were chemically synthesized. Then a portion of the purified genomic DNA from BALL-cell obtained in Example 1-1(a) was subjected to gene amplification similarly as in Example 1-1(a) except that Primers 3 and 4 were replaced for Primers 1 and 2, thus obtaining a DNA fragment of about 850 base pairs with human beta-globin intron region. The DNA fragment was then exposed in usual manner to T4 DNA polymerase for smoothing both ends and inserted in "pBluescript SK (−)", a plasmid vector commercialized by Stratagene Cloning Systems, La Jolla, Calif., U.S.A., which had been cleaved with restriction enzyme Hinc II, to obtain a recombinant DNA which was then introduced in HB101 strain of *Escherichia coli*, proliferated, isolated and purified similarly as in Example 1-1(a). A portion of the recombinant DNA was analyzed by the dideoxy method for nucleic acid sequence in the inserted DNA fragment, confirming that the recombinant DNA contained the nucleic acid sequence reported by Thein et al. Thereafter the recombinant DNA was digested with restriction enzymes Pst I and Xho I and subsequent purification of the digest gave a Pst I-Xho I DNA fragment of 840 base pairs with human beta-globin intron region.

TABLE 3

Primer 3:
5'-GGGTGAGTCTATGGGACCCTTG-3'(SEQ ID NO: 4)

TABLE 4

Primer 4:
5'-AGCTGTGGGAGGAAGATAAGAGG-3'(SEQ ID NO: 5)

EXAMPLE 1-1(c)

Preparation of DNA fragment with poly (A) gene

Plasmid vector pSV2neo (ATCC37149) was digested with restriction enzyme Bgl II, linked with T4 ligase to a Bgl II linker with a nucleic acid sequence as shown in Table 5, further digested with restriction enzyme Bam HI and purified, thus obtaining a Xho I-Bam HI DNA fragment of 320 base pairs with poly (A) gene.

TABLE 5

| Bgl II linker: | 5'-TCGAG | TCTAGA | GCGGCCGC | GGGCCC | A | -3'(SEQ ID NO: 6) |
|---|---|---|---|---|---|---|
| | 3'- C | AGATCT | CGCCGGCG | CCCGGG | TCTAG-5'(SEQ ID NO: 7) | |
| | XhoI | XbaI | NotI | ApaI | BglII | |

EXAMPLE 1-1(d)

Preparation of DNA fragment with M13

A Hgi AI-Pvu II DNA fragment prepared in usual manner with "M13mp18", a phage vector commercialized by Takara Shuzo Co., Ltd., Shiga, Japan, was linked with T4 DNA ligase to a Hgi AI linker with a nucleic acid sequence as shown in Table 6, digested with restriction enzyme Bam HI and purified to obtain a Bam HI-Pvu II DNA fragment of 467 base pairs with M13.

TABLE 6

| Hgi AI linker | | | | |
|---|---|---|---|---|
| 5'- | C GGATCC | GAATTC | GCG-3'(SEQ ID NO: 8) | |
| 3'-TCGTG | CCTAGG | CTTAAG | CGC-5'(SEQ ID NO: 9) | |
| HgiAI | Bam HI | Eco RI | | |

EXAMPLE 1-1(e)

Preparation of DNA fragment with NeoR gene

Plasmid vector pSVneo was digested in usual manner with restriction enzymes Pvu II and Bam HI and subsequent purification of the digest gave a Pvu II-Bam HI DNA fragment of 1,487 base pairs with NeoR gene.

EXAMPLE 1-1(f)

Preparation of DNA fragment with ORI and AmpR genes

Plasmid vector pUC9 (ATCC37252) was digested in usual manner with restriction enzymes Bam HI and Ssp I and the resultant Bam HI-Ssp I DNA fragment was linked with T4 DNA ligase to a Ssp I linker with a nucleic acid sequence as shown in Table 7, digested with restriction enzyme Bgl II and purified, thus obtaining a Bam HI-Bgl II DNA fragment of 2,230 base pairs with both ORI and AmpR genes.

TABLE 7

Ssp I linker: 5'-AATATTA GATCT GAATTC AAGCTT GGCC-3'(SEQ ID NO: 10)
3'-TTATAAT CTAGA CTTAAG TTCGAA CCGG-5'(SEQ ID NO: 11)
    Ssp  I    BglII   Eco RI  HindIII

EXAMPLE 1-1(g)
Preparation of DNA fragment with dhfr gene

Plasmid vector pSV2-dhfr (ATCC37146) was digested in usual manner with restriction enzymes Bam HI and Pvu II and subsequent purification of the digest gave a Bam HI-Pvu II DNA fragment of 1,907 base pairs with dhfr gene.

EXAMPLE 1-1(h)
Preparation of Nru I-Nde I DNA fragment

With reference to the nucleic acid sequence for human cytomegalovirus (HCMV) enhancer reported by Michael Boshart et al. in Cell, Vol. 41, pp. 521–530 (1985), Primers 5 and 6 with nucleic acid sequences as shown in Tables 8 and 9 respectively were chemically synthesized.

TABLE 8

Primer 5:
5'-GCTTCGCGATGTACGGG-3'(SEQ ID NO: 12)

TABLE 9

Primer 6:
5'-CGTACTTGGCATATGATAC-3'(SEQ ID NO: 13)

Separately, DNAs in AD-169 strain of HCMV (ATCC VR-807) were collected, purified in usual manner and subjected to gene amplification by the PCR method in the presence of Primers 5 and 6 and the resultant DNA fragment of about 280 base pairs was exposed to T4 DNA ligase for smoothing both ends and inserted in plasmid vector pUC18 (ATCC37253) which had been cleaved with restriction enzyme Hinc II. The resultant recombinant DNA was introduced in HB101 strain of Escherichia coli, proliferated, collected, purified similarly as in Example 1-1(a) and digested with restriction enzymes Nru I and Nde I and subsequent purification of the digest gave a Nru I-Nde I DNA fragment of 277 base pairs with HCMV gene.

EXAMPLE 1-1(I)
Preparation of Nde I-Hind III DNA fragment

Plasmid vector pUC18 was digested in usual manner with restriction enzymes Nde I and Hind III and subsequent purification of the digest gave a Nde I-Hind III DNA fragment of 214 base pairs.

EXAMPLE 1-1(J)
Preparation of DNA fragment with SVE genes

A2895 strain of SV40 (ATCC VR-305) was proliferated, collected and purified in usual manner. Separately, with reference to the nucleic acid sequence reported by Saltzman et al. in The Papovaviridae, pp.27–98, 1986, Plenum Press, New York, U.S.A., Primers 7 and 8 with nucleic acid sequences as shown in Tables 10 and 11 respectively wherein the SVE region was sandwiched were chemically synthesized. The purified DNA from SV40 was subjected to gene amplification by the PCR method in the presence of these Primers 7 and 8 and the resultant DNA fragment of about 190 base pairs was exposed to T4 DNA polymerase for smoothing both ends and inserted with T4 DNA polymerase in plasmid vector pUC18 which had been cleaved with restriction enzyme Hinc II to obtain a recombinant DNA which was then introduced in HB101 strain of Escherichia coli, proliferated, collected and purified, thus obtaining two types of plasmid vectors "pHSVEB" and "pHSVBE" which differed from each other in coding orientation for the SVE region. Portions of these plasmid vectors were investigated by the dideoxy method for nucleic acid sequence in the inserted DNA fragment, confirming that they contained the nucleic acid sequence reported by Saltzman et al.

TABLE 10

Primer 7:
5'-CTATGGTTGCTGACTAATTGAG-3'(SEQ ID NO: 14)

TABLE 11

Primer 8:
5'-CTGAGGCGGAAAGAACCAGC-3'(SEQ ID NO: 15)

Thereafter the two types of plasmid vectors were digested with restriction enzymes Bam HI and Hind III, purified and inserted in plasmid vector pUC18 which had been cleaved with restriction enzyme Hind III. The resultant recombinant DNA wherein 2 SV40 enhancers were linked in series was digested with restriction enzyme Hind III and inserted with T4 DNA ligase in plasmid vector pHSVEB, which had been cleaved with restriction enzyme Hind III, to obtain a recombinant DNA which was then introduced in HB101 strain of Escherichia coli, proliferated, collected, purified, incompletely digested with restriction enzymes Hind III and Bam HI and purified, thus obtaining a Hind III-Bam HI DNA fragment of 684 base pairs wherein 3 SVE regions were linked in series.

EXAMPLE 1-2
Preparation of recombinant DNA with hEPO DNA

Human kidney carcinoma cell line ACNH (ATCC CRL1611) was proliferated in usual manner and from the proliferated cells were collected mRNAs. Separately with reference to the nucleic acid sequence for hEPO reported by Kenneth Jacobs et al. in Nature, Vol.313, pp.806–810 (1985), Primers 9 and 10 with nucleic acid sequences as shown in Tables 12 and 13 respectively wherein hEPO cDNA region was sandwiched were chemically synthesized and the purified mRNAs were subjected to gene amplification by the PCR method in the presence of these Primers to obtain a cDNA of about 600 base pairs. The cDNA was exposed to T4 DNA ligase for smoothing both ends and inserted in plasmid vector pBluescript SK(−), which had been cleaved with restriction enzyme Sma I, to obtain a recombinant DNA which was then introduced by the competent cell method in HB101 strain of Escherichia coli, proliferated, collected and purified. A portion of the recombinant DNA was investigated by the dideoxy method for nucleic acid sequence in the inserted DNA fragment, confirming that the recombinant DNA contained the nucleic acid sequence reported by Jacobs et al.

TABLE 12

Primer 9:
5'-GCGGAGATGGGGGTGCACGA-3'(SEQ ID NO: 16)

TABLE 13

Primer 10:
5'-CACCTGGTCATCTGTCCCCTG-3'(SEQ ID NO: 17)

The recombinant DNA was digested in usual manner with restriction enzymes Xho I and Not I and the DNA fragment with hEPO cDNA was collected from the digest was inserted between the Xho I and Not I restriction sites in the pHIFP1 prepared in Example 1-1 downstream its HuIFN-alpha2 promoter. The recombinant DNA thus obtained was designated as "pIFPhEPO".

EXAMPLE 2
Preparation of transformant with hEPO DNA

The recombinant DNA pIFPhEPO prepared in Example 1-2 was introduced in BALL-1 cells using "Gene Pulsar", an electroporation apparatus commercialized by Bio-Rad Laboratories, Hercules, Calif., U.S.A., under conditions of 25 microfarads and 450 volts. The cells were then cultured in 5% $CO_2$ incubator at 37° C. for 72 hours, suspended in RPMI 1640 medium (pH7.2) supplemented with 10% (v/v) fetal calf serum to give a cell density of about $4 \times 10^5$ cells/ml and further cultured in 5% $CO_2$ incubator at 37° C. for about one month, followed by collecting and cloning viable cells.

The resultant transformants were suspended in RPMI 1640 medium (pH7.2) supplemented with 10% (v/v) fetal calf serum to give a cell density of about $4 \times 10^5$ cells/ml, added with 100 IU/ml IFN-alpha (BALL-1) commercialized by Hayashibara Biochemical Laboratories, Inc., Okayama, Japan, incubated at 37° C. for additional 3 hours, further added with 50 hemagglutination titers of Sendai virus and further cultured at the same temperature for 15 hours.

Assay of the resultant cultures for hEPO activity revealed that "BE-912", a transformant with the highest expression efficiency, produced about 30 IU hEPO per $4 \times 10^5$ transformant cells. As the control, the same transformant was cultured similarly as above in the absence of Sendai virus, resulting in no hEPO production. This would support that in the transformant of this Example its expression is artificially controllable with external stimuli using IFN-alpha inducers.

In this invention, hEPO activities were first determined by the method which used as criterion $^3$H-thymidine incorporation in spleen cells from mice which had been administered with phenyl hydrazine for induction of anemia in accordance with the method reported by Gerald Krystal in *Experimental Hematology*, Vol.11, No.7, pp.649–660 (1983), then calibrated and represented in terms of the International Unit (U). The standard as used was an hEPO of human urinary origin commercialized by Wako Pure Chemicals Industry Co., Ltd., Osaka, Japan.

EXAMPLE 3
Preparation of recombinant DNA with HuIFN-gamma DNA

Peripheral blood was collected from a healthy volunteer and the lymphocytes were isolated therefrom in usual manner. The lymphocytes were suspended in RPMI 1640 medium (pH7.2) supplemented with 10% (v/v) fetal calf serum to give a cell density of $2.5 \times 10^6$ cells/ml, added with 10 micrograms/ml lentil-lectin and incubated in 5% $CO_2$ incubator at 37° C. for 48 hours. The cells were centrifugally collected from the resultant culture and the mRNAs were collected, purified therefrom in usual manner and amplified by the RT-PCR method similarly as in Example 1-2 for HuIFN-gamma cDNA, after which the resultant cDNAs were prepared into recombinant DNA form by insertion in plasmid vector pBluescript SK(-) similarly as in Example 1-2, introduced in HB101 strain of *Escherichia coli* and proliferated.

Separately with reference to the nucleic acid sequence for HuIFN-gamma cDNA reported by Rik Derynck et al. in *Nucleic Acids Research*, Vol.10, No.12, pp.3,605–3,615 (1982), Probes 1 through 3 with nucleic acid sequences as shown in Tables 14 through 16 respectively were chemically synthesized and labelled with $^{32}$P. By using these Probes, among the above cells of *Escherichia coli* was selected a clone with HuIFN-gamma cDNA which was then proliferated in usual manner, followed by collecting and purifying a recombinant DNA. A portion of the recombinant DNA was investigated by the dideoxy method for nucleic acid sequence of the inserted DNA fragment, confirming that the recombinant DNA contained the nucleic acid sequence reported by Derynck.

TABLE 14

Probe 1:
5'-TGGCTGTTACTGCCAGGACCCATAT-3'(SEQ ID NO: 18)

TABLE 15

Probe 1:
5'-AAACGAGATGACTTCGAAA-3'(SEQ ID NO: 19)

TABLE 16

Probe 1:
5'-CATGAACTCATCCAAGTGA-3'(SEQ ID NO: 20)

Thereafter, in usual manner, the recombinant DNA was digested with restriction enzyme Xho I and Not I and from the resultant digest was collected a DNA fragment with HuIFN-gamma cDNA which was then inserted between the Xho I and Not I restriction sites in the plasmid vector phIFP1 constructed in Example 1-1, thus obtaining a recombinant DNA "pIFPhIFG" wherein HuIFN-gamma cDNA was linked downstream HuIFN-alpha promoter.

EXAMPLE 4
Preparation of transformant with HuIFN-gamma DNA

The recombinant DNA pIFPhIFG obtained in Example 3 was introduced in BALL-1 cells by the electroporation method similarly as in Example 2. The resultant transformants were suspended in RPMI 1640 medium (pH7.2) supplemented with 10% (v/v) fetal calf serum, cultured in 5% $CO_2$ incubator at 37° C. for 72 hours, collected from the resultant culture and washed with a fresh preparation of the same medium. The transformants were then suspended in RPMI 1640 medium (pH7.2) containing 1 mg/ml G-418 and 10% (v/v) fetal calf serum to give a cell density of about $4 \times 10^5$ cells/ml and cultured in 5% $CO_2$ incubator at 37° C. for about one month, followed by collecting and cloning vial cells.

Forty types of transformants thus obtained were separately suspended in RPMI 1640 medium (pH7.2) supplemented with 10% (v/v) fetal calf serum to give a cell density of about $4\times10^5$ cells/ml, added with 100 IU/ml IFN-alpha (BALL-1), cultured at 37° C. for 15 hours, added with about 50 hemagglutination titers/ml of Sendai virus and cultured at the same temperature for additional 15 hours. Assay of the resultant cultures for antiviral activity revealed that "BIG-713", a transformant with the highest expression efficiency, produced about 6,000 IU HuIFN-gamma per $4\times10^5$ transformant cells. As the control, the same transformant was cultured in the absence of Sendai virus similarly as above, resulting in no HuIFN-gamma production. This would support that in the transformant of this Example its expression is artificially controllable with external stimuli using IFN-alpha inducers.

In this invention, HuIFN-gamma activities were first determined by the pigmentation method which used as criterion denaturation of FL cells, a type of human amnion cell line, as caused by sindbis virus in the presence of monoclonal anti-HuIFN-alpha and anti-HuIFN-beta antibodies, then calibrated and represented in terms of the International Unit (IU). The standard as used was HuIFN-gamma preparation (NIH Ga23-901-530) available from the National Institute of Health, U.S.A.

Production of hEPO and HuIFN-gamma using the transformants prepared by the previous embodiments will be explained in conjunction with several Reference Examples.

REFERENCE EXAMPLE 1
Production of hEPO using transformant

The transformant BE-912 obtained in Example 1-2 was suspended in RPMI 1640 medium (pH7.2) supplemented with 10% (v/v) fetal calf serum to give a cell density of about $5\times10^6$ cells/ml and cultured in 5% $CO_2$ incubator at 37° C. for 18 hours. The cells in the resultant culture were centrifugally collected, washed with a fresh preparation of the same medium, resuspended in a fresh preparation of the same medium to give a cell density of about $5\times10^6$ cells/ml, added with 100 IU/ml IFN-alpha (BALL-1), incubated in 5% $CO_2$ incubator at 37° C. for 3 hours, added with 50 hemagglutination titers/ml of Newcastle disease virus and cultured at the same temperature for additional 18 hours. Assay of the resultant culture for EPO activity revealed that about 400 U/ml EPO was produced.

Thereafter, in usual manner, the culture was separated from transformant cells and concentrated, after which the hEPO in the culture was purified with ion exchange chromatography, hydroxyapatite column chromatography and gel filtration chromatography to a specific activity of about $1\times10^5$ U/mg protein. A portion of the purified hEPO was electrophoresed on SDS-polyacrylamide gel and exposed on the gel to periodic acid Schiff reagent, thus a band coincident with EPO activity was stained into red. This suggested that the produced hEPO beared a significant glycosylation.

REFERENCE EXAMPLE 2
Production of hEPO using transformant

The transformant "BE-912" obtained in Example 1-2 was suspended in RPMI 1640 medium (pH7.2) supplemented with 10% (v/v) fetal calf serum to give a cell density of about $5\times10^6$ cells/ml and proliferated similarly as in Reference Example 1. The transformant was then resuspended in physiological saline and subcutaneously implanted by injection in the femora of newborn hamster which had been immunosuppressed in usual manner in an inoculum of about $1\times10^7$ cells/hamster, followed by feeding them in usual manner for 4 weeks. The tumor lumps subcutaneously formed in the hamsters, averaged wet weight of about 15 g/hamster, were extracted and disaggregated in usual manner and the obtained cells were washed with RPMI 1640 medium (pH7.2), suspended in a fresh preparation of the same medium to give a cell density of about $5\times10^6$ cells/ml, added with 100 IU/ml IFN-alpha (BALL-1), incubated in 5% $CO_2$ incubator at 37° C. for 3 hours, further added with 50 hemagglutination titers/ml of Sendai virus and incubated at the same temperature for additional 18 hours. Assay of the resultant culture for EPO activity revealed that about 600 U/ml hEPO was produced.

REFERENCE EXAMPLE 3
Production of HuIFN-gamma using transformant

The transformant BIG-713 obtained in Example 4 was suspended in RPMI 1640 medium (pH7.2) supplemented with 10% (v/v) fetal calf serum to give a cell density of about $4\times10^4$ cells/ml and cultured in 5% $CO_2$ incubator at 37° C. for 15 hours for proliferation. The cells were centrifugally collected from the resultant culture, washed with physiological saline, resuspended in serum-free RPMI 1640 medium (pH7.2) to give a cell density of about $5\times10^6$ cells/ml, added with 100 IU/ml IFN-alpha (BALL-1), incubated in 5% $CO_2$ incubator at 37° C. for 3 hours, further added with 100 hemagglutination titers/ml of Sendai virus and incubated at the same temperature for additional 18 hours. Assay of the resultant culture for antiviral activity revealed that about 80,000 IU/ml HuIFN-gamma was produced.

Thereafter, in usual manner, the culture was separated from transformant cells and concentrated, after which the HuIFN-gamma present in the culture was purified with anti-HuIFN-gamma antibody column chromatography to a specific activity of about $1\times10^7$ IU/mg protein. A portion of the purified HuIFN-gamma was electrophoresed on SDS-polyacrylamide gel and exposed on the gel to periodic acid Schiff reagent, thus a band coincident with antiviral activity was stained into red. This suggested that the produced HuIFN-gamma beared a significant glycosylation.

REFERENCE EXAMPLE 4
Production of HuIFN-gamma using transformant

The transformant BIG-713 obtained in Example 4 was suspended in RPMI 1640 medium (pH7.2) supplemented with 10% (v/v) fetal calf serum to give a cell density of about $4\times10^4$ cells/ml and cultured in 5% $CO_2$ incubator at 37° C. for 15 hours for proliferation. The cells were centrifugally collected from the resultant culture, washed with physiological saline, resuspended in serum-free RPMI 1640 medium (pH7.2) and subcutaneously implanted by injection in the femora of nude mice in an inoculum of about $1\times10^7$ cells/nude mouse. Thereafter the nude mice were fed in usual manner for 5 weeks and the tumor lumps subcutaneously formed in the nude mice, averaged wet weight of about 12 g/nude mice, were extracted and disaggregated.

The transformant cells thus obtained were treated similarly as in Reference Example 3 except that Sendai virus was replaced for Newcastle disease virus, thus about 100,000 IU/ml HuIFN-gamma was produced.

As described above, this invention is to provide a novel recombinant DNA and transformant both utilizing IFN-alpha promoters.

Transformants wherein the recombinant DNA of this invention has been introduced enable artificial control on their polypeptide production by the presence and absence of external stimuli using IFN-alpha inducers. Because of this, when cultured in the absence of IFN-alpha inducers, the transformant of this invention proliferates to maximum level with causing neither damages nor extinction due to polypeptides it produces. While proliferated transformants allow the introduced DNAs to express in maximum level leading to production of objective polypeptides when cultured in turn in the presence of IFN-alpha inducers. Thus according to this invention even polypeptides whose production has been deemed very difficult with conventional recombinant DNA technology can be easily produced in desired amounts.

Further this invention has another merit that it enables efficient production of less dangerous and less toxic polypeptides in desired amounts because in this invention IFN-alpha promoters very strongly work, as well as because even usual IFN-alpha inducers are feasible in production steps for medicines with causing no troubles and then easily removable in the course of purification steps. In particular, even in case that objective polypeptides are such which are very efficacious but originally produced in glycosylated forms and therefore whose production has been deemed very difficult with conventional recombinant DNA technology, this invention does facilitate their production very much. Still further the polypeptides produced in transformants using HuIFN-alpha promoters can be incorporated without care for undesirable side effects in medicines which are principally administered to human because HuIFN-alpha inducers per se are originally present in human body.

This invention, which exhibits such notable effects and functions, can be said to be a significant invention which would be greatly contributive in the art.

We claim:

1. A replicable recombinant DNA molecule comprising a plasmid vector, an interferon-alpha promoter, and a DNA encoding a polypeptide excluding interferon-alpha, said interferon-alpha promoter and said DNA being operably linked as an insertion in said plasmid vector, said recombinant DNA molecule capable of expressing an increased amount of said polypeptide in a mammalian host cell when simultaneously or successively stimulated with an interferon-alpha inducer and an interferon-alpha, said mammalian host cell producing said polypeptide along with interferon-alpha when said mammalian host cell is an interferon-alpha producing cell.

2. The replicable recombinant DNA of claim 1, wherein said interferon-alpha promoter is a human interferon-alpha promoter.

3. The replicable recombinant DNA of claim 1, wherein said interferon-alpha promoter has the nucleic acid sequence of SEQ ID NO:1.

4. The replicable recombinant DNA of claim 1, wherein said plasmid vector carries one or more members selected from the group consisting of a G-418 resistance gene, a methotrexate resistance gene, and an ampicillin resistance gene.

5. The replicable recombinant DNA of claim 1, wherein said plasmid vector is phIFP1.

6. The replicable recombinant DNA of claim 1, wherein said DNA encodes either human erythropoietin or human interferon-gamma.

7. A mammalian host cell transformed with the replicable recombinant DNA of claim 1.

8. The transformed mammalian host cell of claim 7, wherein said interferon-alpha promoter is a human interferon-alpha promoter.

9. The transformed mammalian host cell of claim 7, wherein said interferon-alpha promoter has the nucleic acid sequence of SEQ ID NO:1.

10. The transformed mammalian host cell of claim 7, wherein said plasmid carries one or more members selected from the group consisting of a G-418 resistance gene, a methotrexate resistance gene, and an ampicillin resistance gene.

11. The transformed mammalian host cell of claim 7, wherein said plasmid vector is phIFP1.

12. The transformed mammalian host cell of claim 7, wherein said DNA encodes either human erythropoietin or human interferon-gamma.

13. The transformed mammalian host cell of claim 7, wherein said host cell is a human lymphoblastoid cell.

14. A process for producing a recombinant polypeptide, comprising the steps of:

culturing the transformed mammalian host cell of claim 7 to express a recombinant polypeptide when stimulated with an interferon-alpha inducer; and recovering said expressed recombinant polypeptide from the resultant culture.

15. The process according to claim 7, wherein, in said culturing step, the expression of said recombinant polypeptide is enhanced when said transformed mammalian host cell is simultaneously or successively exposed to an interferon-alpha inducer and interferon-alpha.

16. The process according to claim 14, wherein said culturing step comprises proliferating the transformed mammalian host cell in the absence of an interferon-alpha inducer and then culturing the transformed mammalian host cell in the presence of an interferon-alpha inducer.

* * * * *

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 486 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
CGCCTCTTAT GTACCCACAA AAATCTATTT TCAAAAAAGT TGCTCTAAGA ATATAGTTAT      60
CAAGTTAAGT AAAATGTCAA TAGCCTTTTA ATTTAATTTT TAATTGTTTT ATCATTCTTT     120
GCAATAATAA AACATTAACT TTATACTTTT TAATTTAATG TATAGAATAG AGATATACAT     180
AGGATATGTA AATAGATACA CAGTGTATAT GTGATTAAAA TATAATGGGA GATTCAATCA     240
GAAAAAAGTT TCTAAAAAGG CTCTGGGGTA AAAGAGGAAG GAAACAATAA TGAAAAAAAT     300
GTGGTGAGAA AAACAGCTGA AAACCCATGT AAAGAGTGCA TAAAGAAAGC AAAAAGAGAA     360
GTAGAAAGTA ACACAGGGGC ATTTGGAAAA TGTAAACGAG TATGTTCCCT ATTTAAGGCT     420
AGGCACAAAG CAAGGTCTTC AGAGAACCTG GAGCCTAAGG TTTAGGCTCA CCCATTTCAA     480
CCAGTC                                                                486
```

( 2 ) INFORMATION FOR SEQ ID NO:2:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

```
GGATCCCGCC TCTTATGTAC CCACAAAAAT C                                     31
```

( 2 ) INFORMATION FOR SEQ ID NO:3:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

GACGTCAGAC TGGTTGAAAT GGGTGAGCCT A                              31

( 2 ) INFORMATION FOR SEQ ID NO:4:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

GGGTGAGTCT ATGGGACCCT TG                                        22

( 2 ) INFORMATION FOR SEQ ID NO:5:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

AGCTGTGGGA GGAAGATAAG AGG                                       23

( 2 ) INFORMATION FOR SEQ ID NO:6:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

TCGAGTCTAG AGCGGCCGCG GGCCCA                                    26

( 2 ) INFORMATION FOR SEQ ID NO:7:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

GATCTGGGCC CGCGGCCGCT CTAGAC                                    26

( 2 ) INFORMATION FOR SEQ ID NO:8:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

CGGATCCGAA TTCGCG                                               16

( 2 ) INFORMATION FOR SEQ ID NO:9:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:9:

CGCGAATTCG GATCCGTGCT 20

( 2 ) INFORMATION FOR SEQ ID NO:10:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:10:

AATATTAGAT CTGAATTCAA GCTTGGCC 28

( 2 ) INFORMATION FOR SEQ ID NO:11:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:11:

GGCCAAGCTT GAATTCAGAT CTAATATT 28

( 2 ) INFORMATION FOR SEQ ID NO:12:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:12:

GCTTCGCGAT GTACGGG 17

( 2 ) INFORMATION FOR SEQ ID NO:13:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:13:

CGTACTTGGC ATATGATAC 19

( 2 ) INFORMATION FOR SEQ ID NO:14:

( i ) SEQUENCE CHARACTERISTICS:
    ( A ) LENGTH: 22 base pairs (B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:14:

CTATGGTTGC TGACTAATTG AG  22

(2) INFORMATION FOR SEQ ID NO:15:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:15:

CTGAGGCGGA AAGAACCAGC  20

(2) INFORMATION FOR SEQ ID NO:16:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:16:

GCGGAGATGG GGGTGCACGA  20

(2) INFORMATION FOR SEQ ID NO:17:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:17:

CACCTGGTCA TCTGTCCCCT G  21

(2) INFORMATION FOR SEQ ID NO:18:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:18:

TGGCTGTTAC TGCCAGGACC CATAT  25

(2) INFORMATION FOR SEQ ID NO:19:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: cDNA -continued ( x i ) SEQUENCE DESCRIPTION: SEQ ID NO:19:

AAACGAGATG ACTTCGAAA 19

( 2 ) INFORMATION FOR SEQ ID NO:20:

( i ) SEQUENCE CHARACTERISTICS:
      ( A ) LENGTH: 19 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:20:

CATGAACTCA TCCAAGTGA 19